United States Patent
Namsaraev et al.

(10) Patent No.: US 10,648,021 B2
(45) Date of Patent: *May 12, 2020

(54) DNA LIGATION ON RNA TEMPLATE

(71) Applicant: AFFYMETRIX, INC., Santa Clara, CA (US)

(72) Inventors: Eugeni A. Namsaraev, Sunnyvale, CA (US); Xin Miao, Menlo Park, CA (US); John E. Blume, Sunnyvale, CA (US)

(73) Assignee: AFFYMETRIX, INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/798,238

(22) Filed: Oct. 30, 2017

(65) Prior Publication Data

US 2018/0223346 A1     Aug. 9, 2018

Related U.S. Application Data

(60) Division of application No. 14/313,211, filed on Jun. 24, 2014, now abandoned, which is a continuation of
(Continued)

(51) Int. Cl.
*C12Q 1/68* (2018.01)
*C12Q 1/6837* (2018.01)

(52) U.S. Cl.
CPC ................. *C12Q 1/6837* (2013.01)

(58) Field of Classification Search
CPC .............. C12Q 1/6837; C12Q 2533/107
See application file for complete search history.

(56) References Cited

U.S. PATENT DOCUMENTS

| 5,241,060 A | 8/1993 | Engelhardt et al. |
| 5,866,337 A | 2/1999 | Schon |

(Continued)

FOREIGN PATENT DOCUMENTS

| JP | H04262799 A | 9/1992 |
| JP | H05331185 A | 12/1993 |

(Continued)

OTHER PUBLICATIONS

Armstrong et al., "MLL Translocations Specify a Distinct Gene Expression Profile that Distinguishes a Unique Leukemia," Nature Genetics, 30: 41-47 (2001).

(Continued)

*Primary Examiner* — Betty J Forman
(74) *Attorney, Agent, or Firm* — Affymetrix, Inc.; Jinhee Chang

(57) ABSTRACT

Disclosed are methods and compositions for detection and amplification of nucleic acids, wherein two DNA strands hybridized to an RNA strand are ligated. In one aspect, the disclosed methods include removal of an energy source, such as ATP, upon charging a ligase to form an enzyme-AMP intermediate, and then adding substrate, which results in one complete round of RNA-templated DNA ligation. In another aspect, the ligation reaction is accomplished by use of a mixture of at least two different ligase enzymes. The disclosed methods and compositions for RNA-templated DNA ligation may be particularly useful for detection of RNA sequence variants, for example RNA splice variants, and for quantitative expression analysis.

20 Claims, 3 Drawing Sheets

Specification includes a Sequence Listing.

Related U.S. Application Data application No. 12/690,101, filed on Jan. 19, 2010, now Pat. No. 8,790,873.

(60) Provisional application No. 61/145,466, filed on Jan. 16, 2009.

(56) References Cited

U.S. PATENT DOCUMENTS

| | | | |
|---|---|---|---|
| 5,871,921 A | 2/1999 | Landegren et al. | |
| 5,891,702 A | 4/1999 | Sakakibara et al. | |
| 6,235,472 B1 | 5/2001 | Landegren et al. | |
| 6,344,316 B1 | 2/2002 | Lockhart et al. | |
| 7,504,215 B2 | 3/2009 | Cole et al. | |
| 7,824,863 B2 | 11/2010 | Cole et al. | |
| 8,790,873 B2 * | 7/2014 | Namsaraev | C12Q 1/6837 435/6.1 |
| 2003/0036647 A1 | 2/2003 | Shuman et al. | |
| 2004/0086914 A1 | 5/2004 | Cole et al. | |
| 2004/0106112 A1 | 6/2004 | Nilsson et al. | |
| 2007/0225487 A1 | 9/2007 | Nilsson et al. | |
| 2008/0076118 A1 | 3/2008 | Tooke et al. | |

FOREIGN PATENT DOCUMENTS

| | | |
|---|---|---|
| WO | WO-0104265 A2 | 1/2001 |
| WO | WO-2004007751 A2 | 1/2004 |

OTHER PUBLICATIONS

Atencia et al., "T4 RNA Ligase Catalyzes the Synthesis of Dinucleoside Polyphosphates," European Journal of Biochemistry,261: 802-811 (1999).
Bai, X. et al., "Photocleavage of a 2-nitrobenzyl linker bridging a fluorophore to the 5' end of DNA", Proc Natl Acad Sci, USA, vol. 100, No. 2, 2003, 409-13.
Barany, et al., "Genetic Disease Detection and DNA Amplification Using Cloned Thermostable Ligase", Proceedings of the National Academy of Sciences, vol. 88, Issue 1, 1991 , 189-193.
Bonora et al., "Synthesis and characterization of high-molecular mass polyethylene glycol-conjugated oligonucleotides," Bioconjugate Chemistry, 8: 793-797 (1997).
Cole et al., "Direct labeling of RNA with multiple biotins allows sensitive expression profiling of acute leukemia class predictor genes," Nucleic Acids Research, 32(11): e86 (2004).
England and Uhlenbeck, "3'-Terminal Labelling of RNA with T4 RNA Ligase," Nature, 275: 560-561 (1978).
England and Uhlenbeck, "Enzymatic Oligoribonucleotide Synthesis with T4 RNA Ligase," Biochemistry, 17(11): 2069-2076 (1978).
England, TE, Bruce, AG, and OC Uhlenbeck. Specific labeling of 3' termini of RNA with T4 RNA ligase (1980) Methods Enzym. 65: 65-74.
Fareed et al., "Enzymatic Breakage and Joining of Deoxyribonucleic Acid," J. Biol. Chem 246(4): 925-932 (1971).
Golub et al., "Molecular Classification of Cancer: Class Discovery and Class Prediction by Gene Expression Monitoring," Science, 286: 531-537 (1999).
Harrison and Zimmerman, "Polymer-Stimulated Ligation: Enhanced Ligation of Oligo- and Polynucleotides by T4 RNA Ligase in Polymer Solutions," Nucleic Acids Research, 12(21): 8235-8251 (1984).
Hecht et al., "Chemical Aminoacylation of tRNA's," The Journal of Biological Chemistry, 253(13): 4517-4520 (1978).
Hoffman and McLaughlin, "Synthesis and Reactivity of Intermediates Formed in the T4 RNA Ligase Reaction," Nucleic Acids Research, 15(13): 5289-5303 (1987).
Hsuih et al., "Novel, ligation-dependaent PCR assay for detection of Hepatitis C Virus in Serum," J. of Clinical Microbiology, 34(3): 501-507 (1996).
Igloi, "Nonradioactive Labeling of RNA," Analytical Biochemistry, 233: 124-129 (1996).
Kaufmann et al., "T4 RNA Ligase: Substrate Chain Length Requirements," FEBS Letters, 46(1): 271-275 (1974).
Kleppe et al., "Polynucleotide Ligase-Catalyzed Joining of Deoxyribo-oligonucleotides on Ribopolynucleotide Templates and of Ribo-oligonucleotides on Deoxyribopolynucleotide Templates," Proc. Natl. Acad. Sci., 67(1): 68-73 (1970).
Landegren, et al., "A Ligase-Mediated Gene Detection Techniaue", Science 241, vol. 241, 1988, 1077-1080.
Luo, J et al., "Improving the Fidelity of Thermus thermophilus DNA Ligase", Nuc Acids Res. vol. 24( 14). 1996, pp. 3071-3078.
M. Nilsson, et al., "Padlock Probes: Circularizing Oligonucleotides for Localized DNA Detection," Science, 265:2085-2088 (1994).
McLaughlin et al., "Donor Activation in the T4 RNA Ligase Reaction," Biochemistry, 24: 267-273 (1985).
Miyauchi et al., "Further study of hepatitis C virus RNA detection in formalin-fixed, paraffin embedded liver tisues by ligation-dependent polymerase chain reaction," Pathology International, 48(6): 428-432 (1998).
Nilsson et al., "RNA-templated DNA ligation for transcript analysis," Nucleic Acids Research, 29(2): 578-581 (2001).
Park et al., "Detection of hepatitis C virus RNA using ligation-dependent polymerase chain reaction in formalin-fixed, paraffin-embedded liver tissues," Am. J. Pathology, 149(5): 1485-1491 (1996).
Pedersen et al., "A method for directed evolution and functional cloning of enzymes," Proc. Natl. Acad. Sci., 95(18): 10523-10528 (1998).
Richardson, Ross W. and Gumport, Richard I. Biotin and fluorescent labeling of RNA using T4 RNA ligase. Nucleic Acids Research, vol. 11, No. 18, pp. 6167-6184, 1983.
Romaniuk, E., et al. The Effect of Acceptor Oligoribonucleotide Sequence on the T.sub.4 RNA Ligase Reaction. Eur. J. Biochem, 125, 639-643 (1982).
Sekiguchi and Shuman, "Ligation of RNA-containing duplexes by vaccinia DNA ligase," Biochemistry, 36: 9073-9079 (1997).
Silber et al., "Purification and Properties of Bacteriophage T4-Induced RNA Ligase," Proc. Natl. Acad. Sci., 69(10): 3009-3013 (1972).
Sriskanda and Shuman, "Conserved residues in domain la are required for the reaction of *Escherichia coli* DNA ligase with NAD+," J. Biol. Chem., 277: 9695-9700 (2002).
Sriskanda and Shuman, "Role of nucleotidyl transferase motif V in strand joining by Chlorella virus DNA ligase," J. Biol. Chem., 277: 9661-9667 (2002).
Sriskanda,V. and Shuman,S. (1998) Specificity and fidelity of strand joining by Chlorella virus DNA ligase. Nucleic Acids Res., 26, 3536-3541.
Tessier et al. (1986) "Ligation of single-stranded oligodeoxyribonucleotides by T4 RNA ligase," Anal. Biochem., 158(1):171-178.
Tomkinson and Mackey, "Structure and function of mammalian DNA ligases," Mutation Research, 407(1): 1-9 (1998).
Tong et al., "Biochemical properties of a high fidelity DNA ligase from *Thermus* species AK16D," Nucleic Acids Research, 27(3): 788-794 (1999).
Tyagi, Sanjay et al., "Extremely sensitive, background free gene detection using binary probes and beta replicase", Proceedings of the National Academy of Sciences (PNAS), vol. 93, No. 11, National Academy of Sciences, May 28, 1996, 5395-5400.
Uhlenbeck and Cameron, "Equimolar Addition of Oligoribonucleotides with T4 RNA Ligase," Nucleic Acids Research, 4(1): 85-98 (1977).
V. Sriskanda et al., "Characterization of an ATP-Dependent DNA Ligase From the Thermophilic Archaeon Methanobacterium Thermoautotrophicum", Nucleic Acids Research, 2000, vol. 28, No. 11, pp. 2221-2228.
Wu and Wallace, "Specificity of the nick-closing activity of bacteriophage T4 DNA ligase," Gene, 76(2): 245-254 (1989).

\* cited by examiner

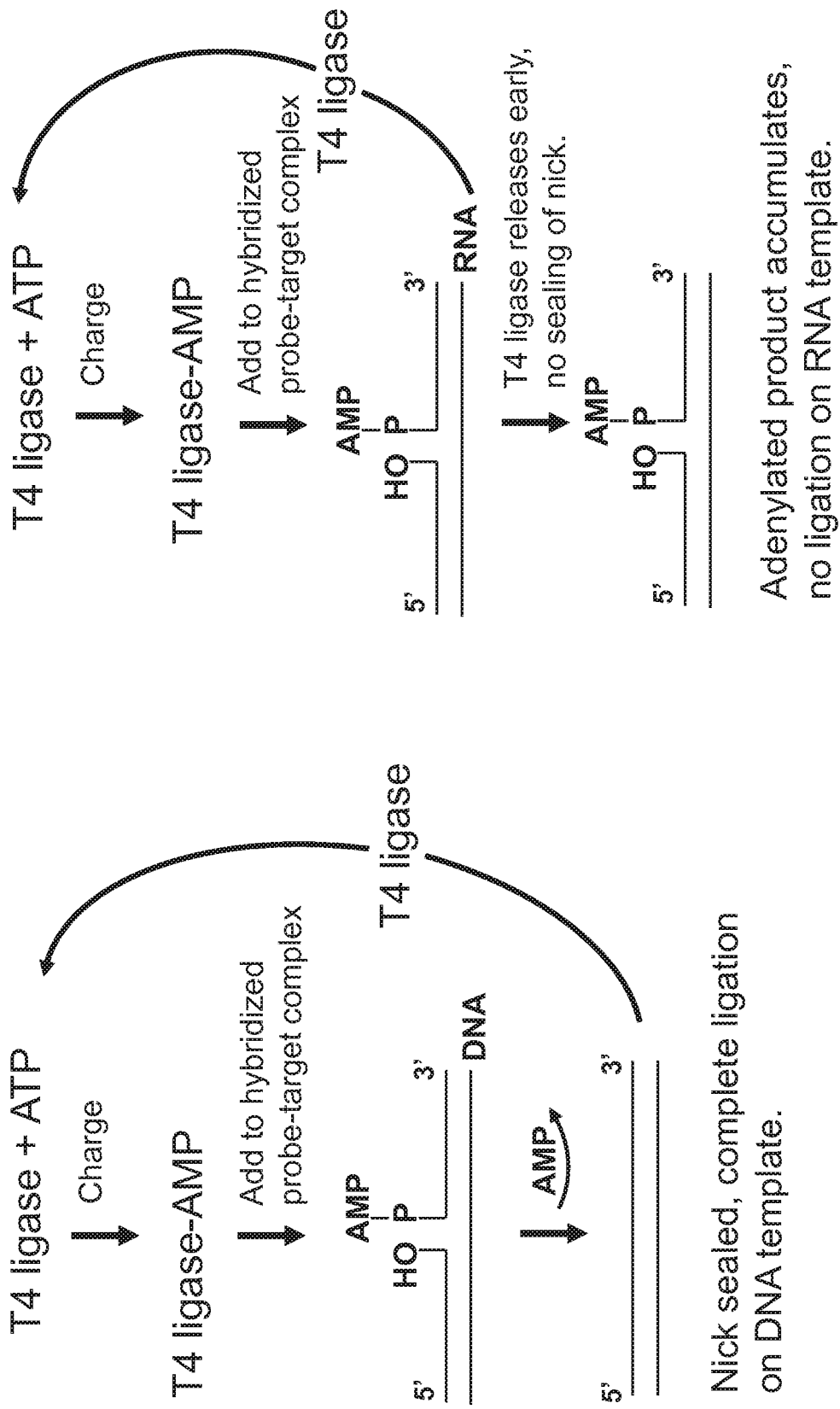

Ligase completes one round of RNA-templated ligation.

Mutant ligase completes the second step of ligation, sealing the nick on adenylated substrate.

DNA LIGATION ON RNA TEMPLATE

RELATED APPLICATIONS

This application is a division of U.S. application Ser. No. 14/313,211 filed Jun. 24, 2014 now abandoned, which is a continuation of U.S. application Ser. No. 12/690,101 filed on Jan. 19, 2010 now U.S. Pat. No. 8,790,873 issued on Jul. 29, 2014 which claims the priority of U.S. Provisional Application No. 61/145,466 filed Jan. 16, 2009 the disclosure of each of which is incorporated herein by reference in their entirety for all purposes.

FIELD OF THE INVENTION

Disclosed are methods related generally to ligation-mediated nucleic acid detection and analysis. Such methods may be performed on a solid support. Disclosed are also methods of gene expression profiling and methods of sequencing of RNA, mediated by ligase enzymes. The methods do not require an intermediate step of generating a cDNA copy of the sequenced RNA by RT-PCR.

REFERENCE TO SEQUENCE LISTING

The Sequence Listing submitted electronically is hereby incorporated by reference. The file is named 3865_1_ST25.txt, the file is 1.68 KB and the date of creation is Jan. 19, 2010.

BACKGROUND OF THE INVENTION

Tools for high-throughput nucleic acid analysis are becoming increasingly important in light of recent advancements in availability of nucleic acid sequence information and genomic data for humans and other organisms. The techniques of ligation-mediated detection of nucleic acids, coupled with hybridization of nucleic acids on arrays are widely used form the basis of genomics applications such as oligonucleotide ligation assay (OLA) (Landegren et al., *Science*, 241:1077 (1998)), ligase chain reaction (Barany, *Proc. Natl. Acad. Sci. USA*, 88:189 (1991)), and ligation of padlock or open circle probes (Nilsson et al., *Science*, 265:2085 (1994)). Ligation-mediated nucleic acid detection methodology relies on the ability of ligases to accurately discriminate between highly homologous nucleotide sequences, differing in some instances only at the terminal nucleotide position. Thus far, most ligation applications involve DNA-templated DNA ligation by a DNA ligase, where both the target nucleic acid and the oligonucleotide probes consist of deoxyribonucleotide polymers. Such applications are particularly useful for generating genomic sequence data and SNP profiling.

RNA-templated DNA ligation is an attractive method for detection of RNA, determination of RNA sequence identity, expression monitoring and transcript analysis. Direct detection of RNA target-DNA probe duplexes (without first converting RNA to cDNA by reverse transcription) has been challenging because a majority of tested DNA ligases fail to ligate nicked DNA on an RNA template. The exception to this is T4 DNA ligase, which is able to ligate nicked DNA hybridized to a RNA strand at a depressed rate.

T4 DNA ligase is an enzyme belonging to the DNA ligase family of enzymes (E.C. 6.5.1.1) which catalyzes the formation of a covalent phosphodiester bond from a free 3' hydroxyl group on one DNA molecule and a free 5' phosphate group of a second, separate DNA molecule, thus covalently linking the two DNA strands together to form a single DNA strand. This activity may also be applied to RNA and is especially useful in molecular genetics where sticky (or blunt) ends of double-stranded DNA (dsDNA) may be fused together with other dsDNA molecules, both products of a restriction enzyme cut, for instance. DNA ligases play critical roles in cell division, in a process called lagging strand DNA replication, as well as cell recovery in the dsDNA break repair mechanism. DNA ligases also play critical roles in normal cellular processes used to generate diversity in the immune system pathways, i.e. during V(D)J recombination. Commercially exploited DNA ligases include the bacteriophage T4 DNA ligase. T4 DNA ligase possesses the basic activity of catalyzing formation of covalent phosphodiester bonds, as described above, but only operates on double-stranded molecules, i.e. DNA/DNA, DNA/RNA hybrids, and RNA/RNA. Like many ligases, T4 DNA ligase activity requires adenosine triphosphate (ATP) as a cofactor. Recombinant T4 DNA ligase, and various mutants thereof, is commercially available.

The ligation reaction catalyzed by DNA ligase occurs in three general steps. First, the ligase enzyme is activated by charging with ATP. Addition of ATP to ligase enzyme causes formation of an intermediate AMP-enzyme species concomitant with hydrolysis of ATP to yield AMP. Second, the charged AMP-enzyme intermediate binds to the dsDNA (or dsRNA, or RNA/DNA complex) and transfers the AMP moiety to the free 5' terminal phosphate, to form a high energy 5'-5' phosphate bond. Third, the enzyme provides the appropriate environment in which the 3' hydroxyl group of the second strand of DNA (or RNA) is able to attack the high energy 5'-5' phosphate bond, thereby forming a covalent phosphodiester bond as a product and releasing ligase enzyme and AMP. Free enzyme does not bind the intermediate high energy 5'-5' phosphate bond species to an appreciable amount. Thus, if the ligase prematurely releases from the duplex after formation of the high energy 5'-5' phosphate bond, the reaction will typically end and the intermediate will not proceed to the final ligated product.

Methods are disclosed herein that provide for efficient RNA-templated DNA ligation.

SUMMARY OF THE INVENTION

Methods for detection of nucleic acids involving ligation of DNA strands hybridized to an RNA strand are disclosed. Such methods are particularly useful, for example, in detection of RNA sequence variants and for quantitative expression analysis. Other plausible non-limiting uses include analysis of viral and ribosomal RNA.

The present methods involve charging T4 DNA ligase with ATP to form an AMP-enzyme intermediate complex. Excess ATP is then removed. Removal of free ATP after the charging step prevents premature cycling of T4 DNA ligase and the accumulation of 5' adenylated (unligatable) product. That is, during RNA-templated DNA ligation, under conditions where ATP is present, T4 DNA ligase will charge, as above, forming the AMP-enzyme complex, then bind the RNA-DNA complex. This is typically followed by premature release of the ligase from the nicked DNA, yielding DNA having a high energy 5'-5' phosphate bond on its free 5' end, which is not a substrate for the DNA ligase reaction. The remaining AMP on the 5' end of the DNA nick prevents any further ligation attempts, since the high energy 5'-5' phosphate bond is not an efficient substrate for the ligase enzyme. The cofactor ATP may be removed by either apyrase or hexokinase treatment. Charging of the ligase in this manner, and addition of near stoichiometric quantities of charged enzyme, allows the DNA ligase enzyme to prepare the RNA-DNA complex for later RNA-templated ligation in an ATP-depleted solution.

Other methods disclosed herein rely on the use of a mixture of two DNA ligase enzymes in the presence of ATP. The first ligase may be, for instance, T4 DNA ligase, or any ligase which produces high energy 5'-5' phosphate bonds at the end of a nicked DNA molecule. The second ligase may be selected from ligase enzymes, or mutants thereof, which are capable of performing only the final step of ligation. In one aspect, the second ligase is a non-native enzyme.

BRIEF DESCRIPTION OF THE FIGURES

FIG. 1 illustrates the differences in DNA vs. RNA-templated ligation using DNA ligase. DNA ligase is capable of efficiently ligating DNA-DNA hybridized complexes. In contrast, DNA ligase often prematurely releases from an RNA-DNA complex after formation of a high energy 5'-5' phosphate bond on the substrate, thus terminating the reaction for that intermediate.

FIG. 2 is a schematic diagram outlining two methods for efficient RNA-templated DNA ligation, as disclosed in the present invention.

DETAILED DESCRIPTION OF THE INVENTION

Figure 2A:
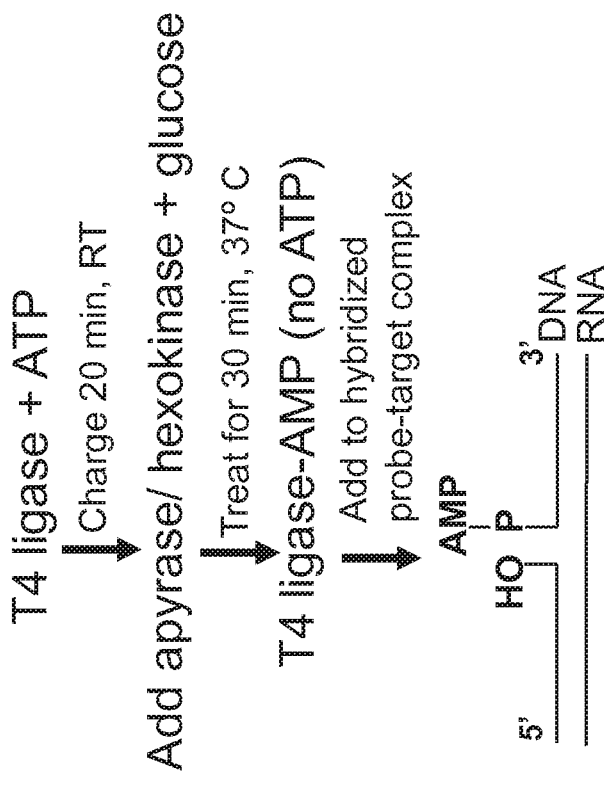
FIG. 2a illustrates a method wherein ligase is first charged with ATP, to form a ligase-AMP species, ATP is then removed and the RNA-templated DNA introduced into the reaction, allowing for completion of one round of RNA-templated ligation.

Reference will now be made in detail to exemplary embodiments. While the disclosed methods and compositions will be described in conjunction with the exemplary embodiments, it will be understood that these exemplary embodiments are not intended to limit the invention. On the contrary, the disclosed methods and compositions are intended to encompass alternatives, modifications and equivalents, which may be included within the spirit and scope of the present application.

The present methods and compositions relate to diverse fields impacted by the nature of molecular interaction, including chemistry, biology, medicine and diagnostics. Methods disclosed herein are advantageous in fields, such as those in which genetic information is required quickly, as in clinical diagnostic laboratories or in large-scale undertakings such as the Human Genome Project.

The present methods and compositions have many embodiments and rely on many patents, applications and other references for details known to those of the art. Therefore, when a patent, application, or other reference is cited or repeated below, it should be understood that the entire disclosure of the document cited is incorporated by reference in its entirety for all purposes as well as for the proposition that is recited. All documents, i.e., publications and patent applications, cited in this disclosure, including the foregoing, are incorporated herein by reference in their entireties for all purposes to the same extent as if each of the individual documents were specifically and individually indicated to be so incorporated herein by reference in its entirety.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of the disclosed methods and compositions may be presented in a range format. It should be understood that when a description is provided in range format, this is merely for convenience and brevity and should not be construed as an inflexible limitation on the scope of the claimed invention(s). Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This understanding applies regardless of the breadth of the range.

The present methods and compositions may employ, unless otherwise indicated, conventional techniques and descriptions of organic chemistry, polymer technology, molecular biology (including recombinant techniques), cell biology, biochemistry, and immunology, which are within the skill of one of skill in the art. Such conventional techniques include polymer array synthesis, hybridization, ligation, and detection of hybridization using a detectable label. Specific illustrations of suitable techniques are provided by reference to the example hereinbelow. However, other equivalent conventional procedures may also be employed. Such conventional techniques and descriptions may be found in standard laboratory manuals, such as *Genome Analysis: A Laboratory Manual* Series (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995), *Biochemistry*, 4th Ed., Freeman, New York, Gait, Oligonucleotide Synthesis: A Practical Approach, (1984), IRL Press, London, Nelson and Cox (2000), Lehninger, *Principles of Biochemistry*, 3$^{rd}$ Ed., W.H. Freeman Pub., New York, N.Y., and Berg et al. (2002), *Biochemistry*, 5$^{th}$ Ed., W.H. Freeman Pub., New York, N.Y. and Berg et al. (2002) *Biochemistry*, 5$^{th}$ Ed., W.H. Freeman Pub., New York, N.Y., all of which are herein incorporated in their entirety by reference for all purposes.

The presently disclosed methods and compositions may employ solid substrates, including arrays in some embodiments. Methods and techniques applicable to polymer (including protein) array synthesis have been described in U.S. Ser. No. 09/536,841 (abandoned), WO 00/58516, U.S. Pat. Nos. 5,143,854, 5,242,974, 5,252,743, 5,324,633, 5,384, 261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, and in PCT Applications Nos. PCT/US99/00730 (International Publication No. WO 99/36760) and PCT/US01/04285

(International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present methods and compositions include, but are not limited to, those that are commercially available from Affymetrix (Santa Clara, Calif.) under the brand name GENECHIP®. Example arrays are shown on the website at affymetrix.com.

Many uses for polymers attached to solid substrates are contemplated herein. These uses include, but are not limited to, gene expression monitoring, profiling, library screening, genotyping and diagnostics. Methods of gene expression monitoring and profiling are described in U.S. Pat. Nos. 5,800,992, 6,013,449, 6,020,135, 6,033,860, 6,040,138, 6,177,248 and 6,309,822. Genotyping and uses therefore are shown in U.S. patent application Ser. No. 10/442,021 (abandoned) and U.S. Pat. Nos. 5,856,092, 6,300,063, 5,858,659, 6,284,460, 6,361,947, 6,368,799, 6,333,179, and 6,872,529. Other uses are described in U.S. Pat. Nos. 5,871,928, 5,902,723, 6,045,996, 5,541,061, and 6,197,506.

Contemplated herein are embodiments employing various sample preparation methods. Prior to, or concurrent with, genotyping, the genomic sample may be amplified by a variety of mechanisms, some of which may employ PCR. (See, for example, *PCR Technology: Principles and Applications for DNA Amplification*, Ed. H. A. Erlich, Freeman Press, NY, N.Y., 1992; *PCR Protocols: A Guide to Methods and Applications*, Eds. Innis, et al., Academic Press, San Diego, Calif., 1990; Mattila et al., *Nucleic Acids Res.*, 19:4967, 1991; Eckert et al., *PCR Methods and Applications*, 1:17, 1991; *PCR*, Eds. McPherson et al., *IRL Press*, Oxford, 1991; and U.S. Pat. Nos. 4,683,202, 4,683,195, 4,800,159 4,965,188, and 5,333,675, each of which is incorporated herein by reference in their entireties for all purposes. The sample may also be amplified on the array. (See, for example, U.S. Pat. No. 6,300,070 and U.S. patent application Ser. No. 09/513,300 (abandoned), all of which are incorporated herein by reference).

Other suitable amplification methods include the ligase chain reaction (LCR) (see, for example, Wu and Wallace, *Genomics*, 4:560 (1989), Landegren et al., *Science*, 241:1077 (1988) and Barringer et al., *Gene*, 89:117 (1990)), transcription amplification (Kwoh et al., *Proc. Natl. Acad. Sci. USA*, 86:1173 (1989) and WO 88/10315), self-sustained sequence replication (Guatelli et al., *Proc. Nat. Acad. Sci. USA*, 87:1874 (1990) and WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245) and nucleic acid based sequence amplification (NABSA). (See also, U.S. Pat. Nos. 5,409,818, 5,554,517, and 6,063,603, each of which is incorporated herein by reference). Other amplification methods that may be used are described in, for instance, U.S. Pat. Nos. 6,582,938, 5,242,794, 5,494,810, and 4,988,617, each of which is incorporated herein by reference.

Additional methods of sample preparation and techniques for reducing the complexity of a nucleic sample are described in Dong et al., *Genome Research*, 11:1418 (2001), U.S. Pat. Nos. 6,361,947, 6,391,592, 6,632,611, 6,872,529 and 6,958,225, and in U.S. patent application Ser. No. 09/916,135 (abandoned).

Methods for conducting polynucleotide hybridization assays have been well developed in the art. Hybridization assay procedures and conditions will vary depending on the application and are selected in accordance with known general binding methods, including those referred to in Maniatis et al., *Molecular Cloning: A Laboratory Manual*, $2^{nd}$ Ed., Cold Spring Harbor, N.Y., (1989); Berger and Kimmel, *Methods in Enzymology, Guide to Molecular Cloning Techniques*, Vol. 152, Academic Press, Inc., San Diego, Calif. (1987); Young and Davism, *Proc. Nat'l. Acad. Sci.*, 80:1194 (1983). Methods and apparatus for performing repeated and controlled hybridization reactions have been described in, for example, U.S. Pat. Nos. 5,871,928, 5,874,219, 6,045,996, 6,386,749, and 6,391,623 each of which are incorporated herein by reference.

Presently contemplated are also methods and compositions employing signal detection of hybridization between ligands. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. No. 10/389,194 (U.S. Patent Application Publication 20040012676), 60/493,495 and in PCT Application PCT/US99/06097 (published as WO99/47964), each of which also is hereby incorporated by reference in its entirety for all purposes.

Embodiments may also employ conventional biology methods, software and systems. Computer software products contemplated herein typically include computer readable medium having computer-executable instructions for performing the logic steps of the presently disclosed methods. Suitable computer readable medium include floppy disk, CD-ROM/DVD/DVD-ROM, hard-disk drive, flash memory, ROM/RAM, magnetic tapes etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The presently disclosed methods may also make use of various computer program products and software for a variety of purposes, such as probe design, management of data, analysis, and instrument operation. (See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170).

Additionally, encompassed herein are embodiments that may include methods for providing genetic information over networks such as the internet, as disclosed in, for instance, U.S. patent application Ser. No. 10/197,621 (U.S. Patent Application Publication No. 20030097222), Ser. No. 10/063,559 (U.S. Patent Application Publication No. 20020183936, abandoned), Ser. No. 10/065,856 (U.S. Patent Application Publication No. 20030100995, abandoned), Ser. No. 10/065,868 (U.S. Patent Application Publication No. 20030120432, abandoned), Ser. No. 10/328,818 (U.S. Patent Application Publication No. 20040002818, abandoned), Ser. No. 10/328,872 (U.S. Patent Application Publication No. 20040126840, abandoned), Ser. No. 10/423,403 (U.S. Patent Application Publication No. 20040049354, abandoned), and 60/482,389 (expired).

A. Definitions

The term "apyrase," as used herein, refers to one or more of a calcium-activated enzyme which possesses ATP-diphosphohydrolase activity and catalyzes the hydrolysis of the gamma phosphate from ATP, and catalyzes the hydrolysis of the beta phosphate from ADP. Apyrases are found in all eukaryotes and some prokaryotic organisms, indicating a preserved role for these enzymes across species. They a distinct phosphohydrolase activity, nucleotide substrate specificity, divalent cation requirement, and sensitivity to inhibitors. (See, Plesner, *Int. Rev. Cytol.*, 158:141 (1995), and Handa and Guidotti, *Biochem. Biophys. Res. Commun.*, 218(3):916 (1996)). In mammals, apyrase is believed to function primarily as an extracellular hydrolase specific for ATP and ADP, which function is important in the inactivation of synaptic ATP molecules following nerve stimulation. (See, Todorov et al., *Nature*, 387(6628):76 (1997)). Apyrase in mammals is also believed to be important in the inhibition of ADP-induced platelet aggregation. (See, Marcus et al., *J. Clin. Invest.*, 99(6):1351 (1997)). Recombinant apyrase is commercially available from New England Biolabs.

The term "array" as used herein refers to an intentionally created collection of molecules which can be prepared either synthetically or biosynthetically. The molecules in the array can be identical or different from each other. The array can assume a variety of formats including, but not limited to, libraries of soluble molecules, and libraries of compounds tethered to resin beads, silica chips, or other solid supports.

The term "complementary" refers to the hybridization or base-pairing between nucleotides or nucleic acids, such as, for instance, that which occurs between the two strands of a double stranded DNA molecule, or between an oligonucleotide primer and a primer binding site on a single stranded nucleic acid to be sequenced or amplified. Complementary nucleotides are pairs of nucleotides having the following identities, generally, A and T (or A and U), or C and G. Two single stranded RNA or DNA molecules are said to be complementary when the nucleotides of one strand, optimally aligned and compared, taking into consideration various nucleotide insertions or deletions, if present, pair with at least about 80% of the nucleotides of the other strand, usually at least about 90% to 95%, and more preferably from about 98 to 100%. Alternatively, complementarity exists when an RNA or DNA polynucleotide will hybridize under selective (or stringent) hybridization conditions to its complement. Typically, selective hybridization will occur when there is at least about 65% complementary over a stretch of at least 14 to 25 nucleotides, preferably at least about 75%, more preferably at least about 90%, or 95%, complementary.

The term "genome" as used herein includes all of the genetic material in the chromosomes of an organism. DNA obtained from the genetic material in the chromosomes of a particular organism is genomic DNA. A genomic library is a collection of clones made from a set of randomly generated overlapping DNA fragments representing the entire genome of an organism.

The term "genotyping" refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position. Thus, the individual may have an A allele and a C allele or alternatively two copies of the A allele or two copies of the C allele. Those individuals who have two copies of the C allele are homozygous for the C allele. Individuals who have two copies of the A allele are homozygous for the A allele. Individuals who have one copy of each allele are heterozygous. The array may be designed to distinguish between each of these three possible outcomes. A polymorphic location may have two or more possible alleles and the array may be designed to distinguish between all possible combinations.

The term "hexokinase" refers to a family of enzymes that catalyze the phosphorylation of a six-carbon sugar, a hexose, to yield a hexose phosphate as the product, in the presence of ATP. Hexokinase enzymes are ubiquitously expressed in eukaryotes and prokaryotes, with several isoforms of the enzyme often found within a single species. The different hexokinase family members share a common ATP-binding site core surrounded by variable domains that determine substrate specificity and other functions, e.g. subcellular localization. There are four mammalian hexokinases, numbered I-IV. Mammalian hexokinase IV (glucokinase) plays a key role in the regulation of glucose metabolism and homeostasis. Hexokinase from *S. cerevisiae* is commercially available, for example, from USB and Sigma-Aldrich.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." Hybridizations are usually performed under stringent conditions, for example, at a salt concentration of no more than 1 M and a temperature of at least 25° C. For example, conditions of 5×SSPE (750 mM NaCl, 50 mM sodium phosphate, 5 mM EDTA, pH 7.4) and a temperature of between 25° C. and 30° C. are suitable for allele-specific probe hybridizations. Hybridization conditions generally suitable for microarrays are described in the Gene Expression Technical Manual, 2004, and the GeneChip Mapping Assay Manual, 2004, available at Affymetrix.com.

The term "label" as used herein refers to, but is not limited to, a luminescent label, a light scattering label or a radioactive label. Fluorescent labels include, inter alia, the commercially available fluorescein phosphoramidites such as Fluoreprime (Pharmacia), Fluoredite (Millipore) and FAM (ABI). (See, U.S. Pat. No. 6,287,778, incorporated herein by reference).

The term "DNA ligase," as used herein, refers to a family of enzymes which catalyze the formation of a covalent phosphodiester bond between two distinct DNA strands, i.e. a ligation reaction. Two prokaryotic DNA ligases, namely the ATP-dependent T4 DNA ligase (isolated from the T4 phage), and the NAD⁺-dependent DNA ligase from *E. coli*, have become indispensable tools in molecular biology applications. Both enzymes catalyze the synthesis of a phosphodiester bond between the 3'-hydroxyl group of one polynucleic acid, and the 5'-phosphoryl group, of a second polynucleic acid, for instance at a nick between the two strands which are both hybridized to a third DNA strand. The mechanism of the ligation reaction catalyzed by this family of enzymes typically requires three enzymatic steps. The initial step involves attack of the α-phosphoryl group of either ATP or NAD⁺, resulting in formation of a ligase-adenylate intermediate (AMP is covalently linked to a lysine residue of the enzyme), and concurrent release of either pyrophosphate ($PP_i$) or nicotinamide mononucleotide (NAD⁺). In the second step of the enzymatic reaction, AMP is transferred to the 5' end of the free 5' phosphate terminus of one DNA strand, to form an intermediate species of DNA-adenylate. In the final step, ligase catalyzes the attack of the DNA-adenylate intermediate species by the 3' hydroxyl group of the second DNA strand, resulting in formation of a phosphodiester bond and sealing of the nick between the two DNA strands, and concurrent release of AMP. RNA ligases, which are a related family of enzymes, catalyze the ligation of nicked RNA ends hybridized on to RNA or DNA in an analogous fashion. T4 DNA ligase is commercially available from at least USB and New England Biolabs.

The terms "mRNA" and "mRNA transcripts," as used herein, include, but are not limited to, pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript, and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of a nucleic acid may be interrupted by non-nucleotide components. Thus the terms nucleoside, nucleotide, deoxynucleoside and deoxynucleotide generally include analogs such as those described herein.

These analogs may possess structural features that are common with a naturally occurring nucleoside or nucleotide, such that when incorporated into a nucleic acid or oligonucleoside sequence, the analogs allow hybridization of the nucleic acid with a naturally occurring nucleic acid sequence in solution. Typically, such analogs are derived from naturally occurring nucleosides and nucleotides by replacing and/or modifying the base, the ribose, or the phosphodiester moiety. These changes incorporated into the analogs can be specifically designed, and therefore function, to stabilize or destabilize hybrid formation, or enhance the specificity of hybridization with a complementary nucleic acid sequence, as desired.

The terms "oligonucleotide" and "polynucleotide" as used herein refer to a nucleic acid ranging from at least 2, preferably at least 8, and more preferably at least 20 nucleotides in length or a compound that specifically hybridizes to a polynucleotide. Polynucleotides contemplated herein include sequences of deoxyribonucleic acid (DNA) or ribonucleic acid (RNA) which may be isolated from natural sources, recombinantly produced or artificially synthesized and mimetics thereof. Further examples of such polynucleotides may be peptide nucleic acid (PNA). Also contemplated are embodiments in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. A biallelic polymorphism has two forms. A triallelic polymorphism has three forms. Single nucleotide polymorphisms (SNPs) are included in polymorphisms. Single nucleotide polymorphisms (SNPs) are positions at which two alternative bases occur at appreciable frequency (>1%) in a given population. SNPs are the most common type of human genetic variation. A polymorphic site is frequently preceded by and followed by highly conserved sequences (e.g., sequences that vary in less than 1/100 or 1/1000 members of the populations).

A SNP may arise due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

The term "probe" as used herein refers to a surface-immobilized or free-in-solution molecule that can be recognized by a particular target. U.S. Pat. No. 6,582,908 provides an example of arrays having all possible combinations of nucleic acid-based probes having a length of 10 bases, and 12 bases or more. In one embodiment, a probe may consist of an open circle molecule, comprising a nucleic acid having left and right arms whose sequences are complementary to the target, and separated by a linker region. Open circle probes are described in, for instance, U.S. Pat. No. 6,858,412, and Hardenbol et al., *Nat. Biotechnol.,* 21(6):673 (2003). In another embodiment, a probe, such as a nucleic acid, may be attached to a microparticle carrying a distinguishable code. Encoded microparticles which can be used for in-solution array assays are described in, for instance, International Patent Application Publication No. WO 2007/081410, and U.S. patent application Ser. No. 11/521,057 (U.S. Patent Application Publication No. 2008/0038559). Examples of nucleic acid probe sequences that may be investigated using the disclosed methods and compositions include, but are not restricted to, those that are complementary to genes encoding agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. (See, U.S. Pat. No. 5,744,305 for exemplary substrates).

The term "target" as used herein refers to a molecule that has an affinity for a given probe. Targets may be naturally occurring or man-made, i.e. synthetic, molecules. Targets may be employed in their unaltered state, or as aggregates with other species. Targets may be attached, covalently or noncovalently, to a binding member, either directly or via a specific binding substance. Examples of targets which can be employed herein include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and cell organelles. Targets are sometimes referred to in the art as anti-probes. As the term "targets" is used herein, no difference in meaning between this term and the term "anti-probe" is intended. A "probe-target complex" is formed when two macromolecules have combined through molecular recognition to form a complex.

B. RNA-templated Ligation

Many disease states are characterized by differences in the expression levels of various genes, either through transcriptional regulation or through copy number changes at the level of genomic DNA. A common method of monitoring gene expression is to detect and quantitate specific RNA transcripts. This may be accomplished by employing microarray technology. However, closely related RNA sequences pose a challenge for expression analysis using microarray technology because the expression of, and quantity of, mRNA of different genes vary dramatically and under certain conditions, can compete with each other for probe hybridization. In other words, related RNA sequences that are not perfectly complementary to the probe sequence, but which are expressed at a much higher level than the target RNA, can potentially hybridize to the probe under standard hybridization conditions, thereby skewing results of hybridization-based assays. In addition to mRNA transcript detection and analysis, the disclosed methods can be used for detection of all ribonucleic acids from all sources (for example, ribosomal RNA and viral RNA).

Further, it is clear that genotyping of polymorphisms in RNA, such as single nucleotide polymorphisms (SNPs), provides useful information in analysis of disease physiology and progression. That is, alternative splicing at the mRNA level is known to lead to different translation products that possess different activities. These differences may correlate to various disease symptoms. Thus, research is now being directed at detecting various alternative splicing events. The ability to detect and quantitate such alternative splicing events may be achieved through the following methods and compositions. For instance, in one embodiment, DNA probes may be immobile onto an array. The DNA probes could be complementary to, for instance the last (downstream-most) exon of an mRNA molecule. All mRNA transcripts possessing that exon will hybridize to the immobilized DNA probe. Following this hybridization, a second DNA probe may be added which is complementary to one of several possible alternative splice sequences in the mRNA, upstream of the sequence hybridized to the immobilized probe. The mRNA transcript will now be hybridized to, and serving as a template for, the two DNA probes, one of which is immobilized. DNA polymerase may then be used to ligate the two probes together, if the second DNA probe hybridizes to the mRNA transcript. The second DNA probe could include a detectable label. Ligation of the second probe to the first probe will therefore leave a detectable label covalently bound to the array and after washing steps, it will be detected, thus indicating the presence of the alternative splice variant.

One of skill in the art will be familiar with such methodologies and understand that many variations exist on this type of assay. For instance, molecular inversion probes (MIPs) may also be used in this manner to detect mRNA splice variants. Such assays may even be performed directly on Formalin-Fixed, Paraffin-Embedded (FFPE) samples or fresh-frozen samples.

DNA ligases are able to distinguish single nucleotide variations among DNA sequences and therefore may be exploited in such expression profiling analyses. DNA ligases are relatively inefficient in ligating two nucleic acid sequences possessing non-complementary termini. This property of the ligase enzyme has been exploited in an assay termed the oligonucleotide ligation assay (OLA). (See, Landegren et al., *Science,* 241:1077 (1998); Wu, D. Y. & Wallace, R. B. *Gene* 76, 245-254 (1989); Luo, J., Bergstrom, D. E. & Barany, F., *Nucleic Acids Res.* 24, 3071-3078 (1996); and Tong, J., Cao, W. & Barany, F., *Nucleic Acids Res.* 27, 788-794 (1999)). Another method exploiting this property of the ligase is termed the ligase chain reaction. (See, Barany, *Proc. Nat'l. Acad. Sci. USA,* 88:189 (1991)). However, direct detection of RNA target-DNA probe duplexes (without first converting RNA to cDNA by reverse transcription) is difficult given that a majority of DNA ligases fail to ligate nicked DNA hybridized to an RNA template.

Presently, only T4 DNA ligase has been shown to catalyze the ligation of DNA oligonucleotides hybridized to RNA templates. However, this function of T4 DNA ligase is substantially reduced in catalytic efficiency as compared to its catalyzation of DNA-templated reactions. (See, Kleppe et al., *Proc. Nat'l. Acad. Sci. USA,* 67:68 (1970), and Fareed et al., *J. Biol. Chem.,* 246:925 (1971)).

It has previously been reported that under low salt, particularly monovalent cations, and low ATP concentrations, high concentrations of T4 DNA ligase efficiently join DNA oligonucleotides hybridized in juxtaposition on RNA target strands. See, US Patent Pub. 20070225487, which is incorporated herein by reference in its entirety.

It is also known that some of the ATP dependent DNA ligases in eukaryotes and eucaryotic virus can use RNA as a template for DNA ligation (see, Tomkinson, A. E. and Mackey, Z. B. *Mutation Res.* 407 1-9 (1998), Sekiguchi, J. and Shuman, S. *Biochemistry* 36 9073-9079 (1997), and Sriskanda, V. and Shuman, S. *Nucleic Acids Res.* 26 3536-3541 (1998)).

However, it is not know how efficient the reaction is using these enzymes, and eukaryotic enzymes have not been used for gene analytic assays. Also ATP-dependent DNA ligases from thermophilic archeon such as *Methanobacterium thermoautotrophicum* (Sriskanda, V., et al. *Nucleic Acids Res* 28 2221-2228. (2000)) can join DNA oligonucleotides. The general features of the detection methods described herein should be generally applicable for all DNA ligases.

RNA-templated ligation of DNA probes has been used to generate molecules, amplifiable by PCR via general sequences present at the remote ends of a pair of ligation probes (Hsuih, T. C. H. et al. *J. Clin. Microbiol.* 34, 501-507 (1996). The method has been applied to detect viral RNA extracted from clinical and archival specimens with increased sensitivity compared to nested RT-PCR (Park, Y. N. et al., *Am. J Pathology* 149, 1485-1491 (1996); Miyauchi, I., Moriyama, M., Zhang, D. Y. & Abe, K., *Path. Int.* 48, 428-432 (1998)). RNA-templated ligation of RNA probes has been used for detection of transcripts in experiments where ligation products were amplified by the Qb replicase (Tyagi, S., Landegren, U., Tazi, M., Lizardi, P. M. & Kramer, F. R., *Proc. Natl. Acad. Sci. USA* 93, 5395-5400 (1996). RNA-templated ligation of either DNA or RNA probes can thus substitute for a reverse transcription (RT) step before amplification.

T4 DNA ligase catalyzes DNA ligation in three steps. First, the enzyme is activated through ATP hydrolysis, resulting in covalent addition of AMP to the enzyme. This intermediate enzyme species then binds to a nicked DNA site. Second, after binding to the nicked DNA site, the ligase transfers AMP to the phosphate at the 5' end of the nick, forming an intermediate product possessing a 5' to 5' pyrophosphate bond. Third, the ligase catalyzes formation of a phosphodiester bond by attack of the intermediate 5' to 5' pyrophosphate bond by the OH group of the 3' end of the second strand of DNA, resulting in release of the ligase and AMP.

In RNA-templated ligation, T4 DNA ligase will prematurely release from the nicked DNA before the final step, leaving the 5' to 5' pyrophosphate bond intermediate species. Released T4 DNA ligase then re-charges itself using ATP, preventing the enzyme-AMP intermediate species from completing the final step of the reaction, ultimately yielding an accumulation of 5' to 5' pyrophosphate bond intermediate product. It has been shown that incubation of the substrate with T4 DNA ligase at a very low ATP concentration improves the ligation efficiency of T4 DNA ligase, but the reaction proceeds very slowly and requires relatively large amounts of enzyme. (See, Nilsson et al., *Nucleic Acids Res.,* 29(2):578 (2001). Moreover, the longer (2 hour or more) incubation period combined with the necessary determination of an optimum ATP concentration can be an obstacle for a number of applications.

Although RNA-templated DNA ligation promises to be an attractive method for expression monitoring and transcript analysis, the poor ligation efficiency of T4 DNA ligase on RNA templates has hampered the development of methodologies relying on ligation-mediated detection and analysis of ribonucleic acids. Methods are disclosed that provide for efficient RNA-templated DNA ligation.

In one embodiment, as depicted in FIG. 2a, the disclosed methods involve charging T4 DNA ligase with ATP to form the charged enzyme-AMP species, followed by removal of excess or unused ATP to prevent premature cycling of T4 DNA ligase and the accumulation of the 5' to 5' pyrophosphate bond intermediate product. Removal of free ATP by either addition of apyrase or hexokinase, under proper buffer conditions, for instance, pushes the reaction in the direction of a single round of T4 DNA ligase-mediated ligation. Of course, any known method of ATP depletion may be employed for this purpose. Depletion of ATP after charging of the enzyme, by any means which does not further interfere with the ligation reaction, will be suitable in the present method.

Figure 2B:
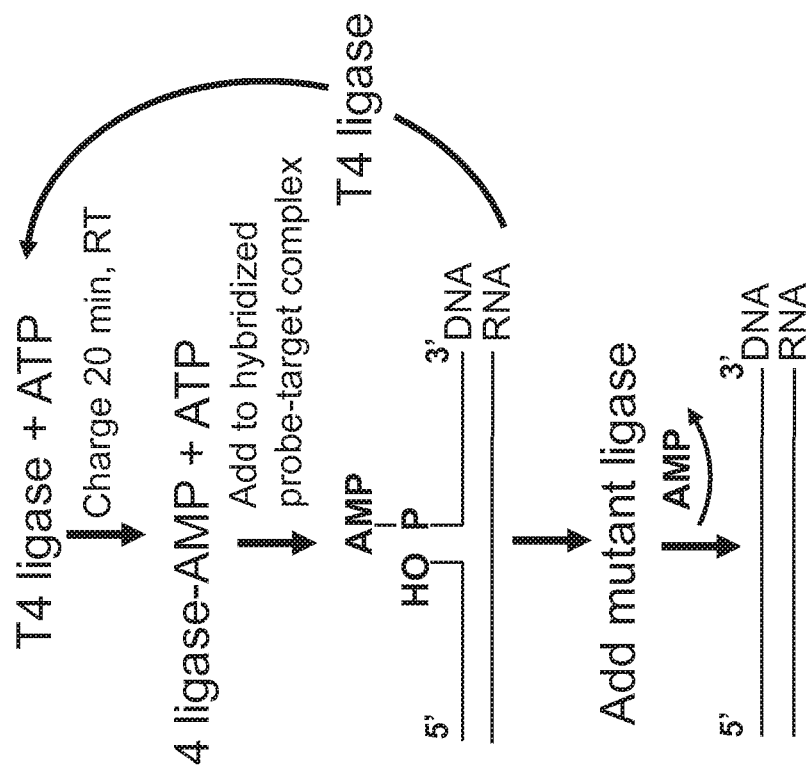
FIG. 2b illustrates a similar method in which RNA-templated DNA ligation is achieved using a mixture of two different ligase enzymes.

In another embodiment, depicted in FIG. 2b, the disclosed methods may employ a mixture of at least two ligases in the presence of ATP. In this embodiment, the first ligase may be, for instance, T4 DNA ligase, or another ligase capable of producing 5' to 5' pyrophosphate bond product intermediates. The second ligase employed in this embodiment may be any of a number of mutant forms of ligase which catalyze the final step of ligation, i.e. formation of the desired phosphodiester bond between the two strands of DNA template on the RNA molecule, by consumption of the 5' to 5' pyrophosphate bond on the terminus of the first strand of DNA and the terminal hydroxyl group from the second strand of DNA. Mutant ligases that are unable to charge with AMP, i.e. form the intermediate enzyme-AMP complex, but retain the catalytic activity of formation of the covalent phosphodiester bond between the two DNA strands have been described. Such mutant ligase enzymes include, but are not limited to, several point mutants and amino-terminal truncation mutants of the *E. coli* NAD$^+$-dependent DNA ligase. (See, Sriskanda and Shuman, *J. Biol. Chem.,* 277: 9685 (2002)). In this embodiment, multiple different ligases may be utilized for the second ligase, thus the reaction may comprise as many as three different ligases, or four different ligases, or five different ligases, or more. The number of ligases utilized in the reaction mixture is not constrained, so long as the ligases possess the activity required to complete the reaction.

The following list of examples is provided for illustrative purposes only. While the present disclosure is intended to encompass these examples, it will be clear to one of skill in the art that these are non-limiting examples and that many modifications may be made to the examples while still maintaining subject matter within the scope of the present application. For instance, the following methods may be utilized in a series of steps, comprising intermediate steps, steps before and after the provided methods, which further treat and/or prepare the nucleic acids utilized therein. For instance, nucleic acids used herein may also be concurrently or subsequently utilized in microarray analyses, further PCR or transformation reactions, etc. Therefore, these examples are non-limiting.

Detection of ligation may be conducted by many means. For instance, detectable labels may be added to substrate nucleotides. The incorporation of these detectable labels into the ligated product may be measured. Detectable labels may include, but are not limited to, use of fluorescent labels, radioactive labels, phosphorescent labels, etc. Ligation may also be measured by detecting a shift in the substrate band in a gel-shift assay. There exist many means of detecting such ligation events. One of skill in the art will know how to modify and incorporate such means of detection in the context of the present methods and reagents. Such means of detection are incorporated herein for the purpose of measuring the ligation event.

EXAMPLES

Example 1

RNA-Templated Ligation Using Hexokinase Treatment to Eliminate Free ATP

Experimental design involves use of a padlock-type assay where linearized DNA is annealed at two positions onto a linearized RNA template. Padlock probe assays, design and methodologies are disclosed in, for instance, U.S. Pat. Nos. 5,871,921, 6,235,472, 5,866,337, and Japanese patent JP 4-262799, the disclosures of which are incorporated herein by reference in their entirety. Thus, when DNA polymerase is added, and the assay is successful, the enzyme ligates the two ends of the DNA, forming a circularized, single-stranded DNA molecule which may be assayed by gel shift assay or any other means.

In the present experiment, RNA template was prepared from linearized Tch2, H4 or H5 plasmid DNA by in vitro transcription using Ambion's Megascript kit. The TCH2 gene is an *Arabidopsis thaliana* gene encoding a calcium ion binding protein. Four padlock probes (probe sequences may be found in Table 1) were designed, having the sequences shown in Table 1. Thus, in the 5' to 3' direction, the sequence for the first padlock would be as follows: 5'-probe 1b-bridge-probe 1a-3'. Probes 2-4 are similarly arranged in sequence. As is customary in MIP probes, the bridging sequences may comprise the following elements: a first universal PCR primer site, a depyrimidination site (to invert and/or linearize the MIP probe) including the sequence UUU as a uracil DNA glycosylase site, a second universal PCR primer site, a detectably labeled nucleotide for quantitation, a barcode/tag sequence, a DraI restriction site (or any restriction site to release the barcode sequence).

TABLE 1

| Probe # | SEQ ID NO. | Sequences | bp |
|---|---|---|---|
| 1a | 1 | GGCCAGTGCTGGAGTTCGCACGCTATA TTTAAAAGCATCACCAGAAGAAACAG | 53 |
| 1b | 2 | TAACGATGATGAAACAATTCGACCTGT CCACG | 32 |
| 2a | 3 | GGCCAGTGCTGGAGTTCGCACGCTATA TTTAAATCAACAATGTCATCGAAGAA | 53 |
| 2b | 4 | AAATCTCCGTCGACGAGCTCGTCCACG | 27 |
| 3a | 5 | GGCCAGTGCTGGAGTTCGCACGCTATA TTTAAAGGACGACATCAAAAAAGTCT | 53 |
| 3b | 6 | TCCAACGATTCGACAAAAACGTCCACG | 27 |

TABLE 1-continued

| Probe # | SEQ ID NO. | Sequences | bp |
|---|---|---|---|
| 4a | 7 | GGCCAGTGCTGGAGTTCGCACGCTATA TTTAAAAAATCTCCGTCGACGAGCTC | 53 |
| 4b | 8 | AAAGAAGTGATCCGCGCTCTGTCCACG | 27 |

T4 DNA ligase was charged for 20 minutes at room temperature in the presence of ATP. ATP depletion mix was added to the charging mix and the reaction proceeded for another 30 minutes at 37° C. to remove remaining free ATP. In the meantime, RNA/probe mixes were heated to 80° C. for 3 minutes, cooled to 46° C., and then RNAse inhibitors were added followed by 20-minute incubation at 46° C. 5 µl of RNA/probe mix was combined with 5 µl of charged ligase mix, and incubated at 37° C. for 30 minutes, 1 hour, or 2 hours. Ligation reactions were stopped by adding an equal amount of formamide stop solution, and heating to 95° C. for 3 minutes, followed by cooling on ice. The ligated samples were loaded onto an 8% sequencing gel, and resolved ligation products were visualized by SYBR green or ethidium bromide staining. Table 2 provides buffer compositions.

TABLE 2

| ATP/Ligase Charging Mix | | ATP Depletion Mix | |
|---|---|---|---|
| Ingredient | Vol (µl) | Ingredient | Vol (µl) |
| ATP (2 mM) | 2.5 | Hexokinase (10 U/µl) | 2 |
| T4 DNA ligase (2000 U/µl) | 4 | 200 mM glucose | 25 |
| H$_2$O | 2.5 | RNAse inhibitor | 2 |
| 10 X rxn buffer | 1 | H$_2$O | 6 |
| | | 10 X rxn buffer | 5 |
| | | Charging mix | 10 |
| Total | 10 | Total | 50 |

| RNA/Probe 1 Mix | | RNA/Probe 2 Mix | |
|---|---|---|---|
| Ingredient | Vol (µl) | Ingredient | Vol (µl) |
| probe 1 (500 nM) | 0.84 | probe 2 (792 nM) | 0.55 |
| RNA (5.3 uM) | 0.63 | RNA (5.3 uM) | 0.63 |
| RNAse inhibitor | 3 | RNAse inhibitor | 3 |
| H$_2$O | 15.43 | H$_2$O | 15.74 |
| Total | 21 | Total | 21 |

Example 2

RNA-Templated Ligation Using Apyrase Treatment to Deplete Free ATP

The experiment was conducted as described in Example 1, except that the ATP depleting mix consisted of 1 µl of apyrase enzyme (500 mU/µl), 5 µl of 10× reaction buffer, and 34 µl of distilled water instead of hexokinase enzyme. The ATP depleting mix was added to 10 µl of charging mix, as in Example 1, and incubated for 30 minutes at room temperature. The ATP concentration in the charging mix was either 500 µM or 200 µM.

Example 3

RNA-Templated Ligation Using a Mixture of at Least Two Ligases

Charging of T4 ligase and ligation steps may be conducted as described in Example 1, using RNA/probe mixes identical to those in Example 1. Following a 1 hour ligation with T4 ligase in the presence of ATP, NAD⁺-dependent mutant ligase and NAD⁺ may be added to the ligation reaction. For example, *E. coli* LigA point mutants Y22A, D32A and D36A, may be generated from wild-type LigA plasmid DNA by site-directed mutagenesis, using Stratagene's QuickChange kit or a similar product. An amino-terminal truncated LigA construct may also be generated using standard PCR and subcloning approaches. One or more different mutants of LigA, as described above, may be utilized in the present example as the "NAD⁺-dependent mutant ligase." The ligation products will be resolved and visualized as described in example 1.

Example 4

PCR of RNA-Templated Ligation of Padlock Probes

Figure 3:
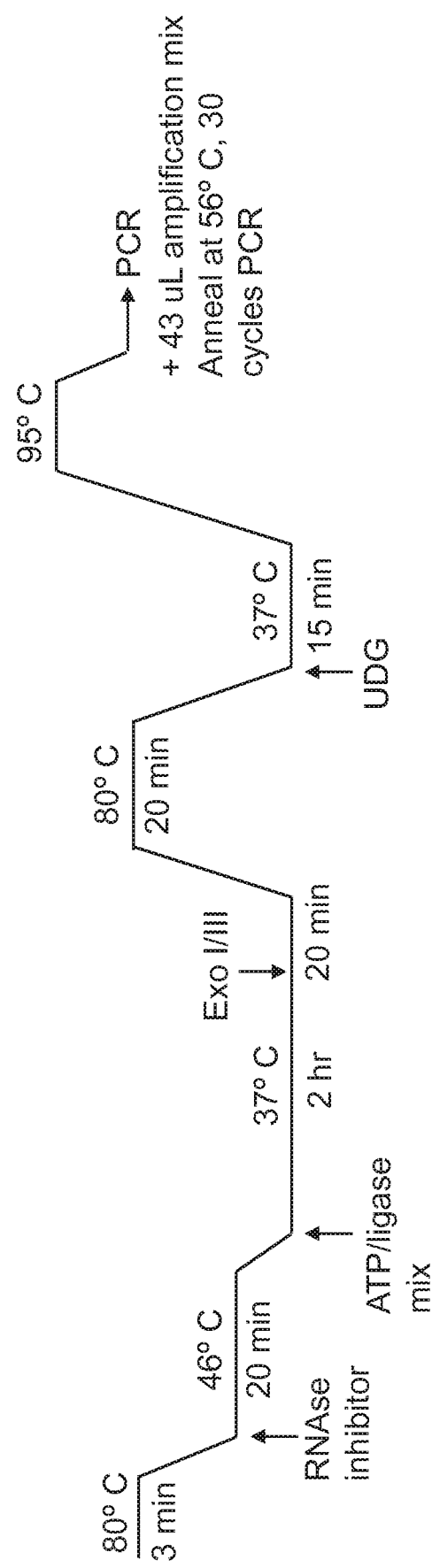
FIG. 3 illustrates a step-by-step outline of a method wherein RNA-templated ligation of padlock probes is followed by PCR.

The experimental setup and timeline for the present Example 4 is illustrated in FIG. 3. This method uses padlock probes with the same sequences as listed above. Probe and RNA target concentrations in the annealing mix were 40 nM and 160 nM, respectively. Probe concentrations relative to RNA concentrations may be from 100:8, respectively to about 10:8, respectively. Concentrations may be from pM to nM depending on the amount needed for signal detection or visualization. Charging of ligase and ATP removal by apyrase treatment was performed as described above in Examples 1 and 2. Following 2 hours of ligation at 37° C., a sufficient amount of Exonuclease I (ExoI) and Exonuclease III (ExoIII), i.e. about 2 µl, were added and the reaction was further incubated at 37° C. for 20 minutes, to digest unligated probe. Following inactivation of ExoI and ExoIII by incubation at 80° C. for 20 minutes, 5 µl of uracil-DNA glycosylase was added and the sample incubated at 37° C. for 15 minutes, to cleave the ligated circular padlock probe, followed by heat inactivation and 30 cycles of PCR.

What is claimed is:

1. A method for detecting a plurality of target nucleic acids from a nucleic acid sample, comprising:
   a) contacting a DNA array-bound probe with:
   (i) a DNA interrogation probe, and
   (ii) a nucleic acid sample comprising at least one target nucleic acid of RNA,
   wherein the array-bound probe and the interrogation probe hybridize to the target nucleic acid such that the array-bound probe and the interrogation probe are directly adjacent to one another, and wherein the interrogation probe contains a detectable label;
   b) adding an effective amount of ATP to a solution of at least two different DNA ligase enzymes,
   wherein the at least two different DNA ligase enzymes comprise a first ligase, which can form a DNA ligase-AMP intermediate complex, and a second ligase, which is a mutant ligase unable to form a DNA ligase-AMP intermediate complex;
   c) depleting ATP from the solution of at least two different DNA ligase enzymes;
   d) adding the solution of at least two different DNA ligase enzymes to step a), thereby ligating the array-bound probe and the interrogation probe; and
   e) detecting the ligated product.

2. The method according to claim 1, wherein the first ligase is T4 DNA ligase.

3. The method according to claim 1, wherein the second ligase is E. coli NAD+-dependent ligase LigA which comprises a point mutant or an amino terminal truncation.

4. The method according to claim 1, wherein the second ligase is an E. coli NAD+-dependent ligase LigA mutant selected from the group consisting of: Y22A, D32A and D36A.

5. The method of claim 1, wherein ATP depletion is accomplished by adding an effective amount of apyrase.

6. The method of claim 1, wherein ATP depletion is accomplished by adding an effective amount of hexokinase.

7. A method of detecting a plurality of target nucleic acids from a nucleic acid sample, comprising:
   a) contacting an open circle DNA probe with a nucleic acid sample comprising at least one target nucleic acid of RNA, wherein the open circle probe comprises a 5' end and a 3' end, and wherein the open circle probe contains a detectable label;
   b) adding an effective amount of ATP to a solution of at least two different DNA ligase enzymes,
   wherein the at least two different DNA ligase enzymes comprise at least a first ligase, which can form a DNA ligase-AMP intermediate complex, and at least a second ligase, which is a mutant ligase unable to form a DNA ligase-AMP intermediate complex;
   c) depleting ATP from the solution of at least two different DNA ligase enzymes;
   d) adding the solution of DNA ligase-AMP intermediate to step a), thereby ligating the 5' end of the open circle probe to the 3' end of the open circle probe; and
   e) detecting the ligated product.

8. The method according to claim 7, wherein ATP depletion is accomplished by adding an effective amount of apyrase.

9. The method according to claim 8, wherein the effective amount of apyrase is about 10 mU apyrase per µl.

10. The method according to claim 7, wherein ATP depletion is accomplished by adding an effective amount of hexokinase.

11. The method according to claim 10, wherein the effective amount of hexokinase is about 0.4 U hexokinase per µl.

12. The method according to claim 7, wherein the first ligase is T4 DNA ligase.

13. The method according to claim 7, wherein the second ligase is *E. coli* NAD+-dependent ligase LigA which comprises a point mutant or an amino terminal truncation.

14. The method according to claim 7, wherein the second ligase is an *E. coli* NAD+-dependent ligase LigA mutant selected from the group consisting of: Y22A, D32A and D36A.

15. A method for detecting a plurality of target nucleic acids from a nucleic acid sample, comprising:
   a) contacting a DNA array-bound probe with:
      (i) a DNA interrogation probe, and
      (ii) a nucleic acid sample comprising at least one target nucleic acid of DNA,
   wherein the array-bound probe and the interrogation probe hybridize to the target nucleic acid such that the array-bound probe and the interrogation probe are directly adjacent to one another, and wherein the interrogation probe contains a detectable label;
   b) adding an effective amount of ATP to a solution of at least two different DNA ligase enzymes,
   wherein the at least two different DNA ligase enzymes comprise at least a first ligase, which can form a DNA ligase-AMP intermediate complex, and at least a second ligase, which is a mutant ligase unable to form a DNA ligase-AMP intermediate complex;
   c) depleting ATP from the solution of at least two different DNA ligase enzymes;
   d) adding the solution of at least two different DNA ligase enzymes to step a), thereby ligating the array-bound probe to the interrogation probe; and
   e) detecting the ligated product.

16. The method according to claim 15, wherein the first ligase is T4 DNA ligase.

17. The method according to claim 15, wherein the second ligase is *E. coli* NAD+-dependent ligase LigA which comprises a point mutant or an amino terminal truncation.

18. The method according to claim 15, wherein the second ligase is an *E. coli* NAD+-dependent ligase LigA mutant selected from the group consisting of: Y22A, D32A and D36A.

19. The method of claim 15, wherein ATP depletion is accomplished by adding an effective amount of apyrase.

20. The method of claim 15, wherein ATP depletion is accomplished by adding an effective amount of hexokinase.

* * * * *

SEQUENCE LISTING

```
<160> NUMBER OF SEQ ID NOS: 8

<210> SEQ ID NO 1
<211> LENGTH: 53
<212> TYPE: DNA
<213> ORGANISM: Artificial sequence
<220> FEATURE:
<223> OTHER INFORMATION: Synthetic

<400> SEQUENCE: 1
ggccagtgct ggagttcgca cgctatattt aaaagcatca ccagaagaaa cag         53

<210> SEQ ID NO 2
<211> LENGTH: 32
<212> TYPE: DNA
<213> ORGANISM: Artificial sequence
<220> FEATURE:
<223> OTHER INFORMATION: Synthetic

<400> SEQUENCE: 2
taacgatgat gaaacaattc gacctgtcca cg                                32

<210> SEQ ID NO 3
<211> LENGTH: 53
<212> TYPE: DNA
<213> ORGANISM: Artificial sequence
<220> FEATURE:
<223> OTHER INFORMATION: Synthetic

<400> SEQUENCE: 3
ggccagtgct ggagttcgca cgctatattt aaatcaacaa tgtcatcgaa gaa         53

<210> SEQ ID NO 4
<211> LENGTH: 27
<212> TYPE: DNA
<213> ORGANISM: Artificial sequence
<220> FEATURE:
<223> OTHER INFORMATION: Synthetic

<400> SEQUENCE: 4
aaatctccgt cgacgagctc gtccacg                                      27

<210> SEQ ID NO 5
<211> LENGTH: 53
<212> TYPE: DNA
<213> ORGANISM: Artificial sequence
```

```
<220> FEATURE:
<223> OTHER INFORMATION: Synthetic

<400> SEQUENCE: 5
ggccagtgct ggagttcgca cgctatattt aaaggacgac atcaaaaaag tct        53

<210> SEQ ID NO 6
<211> LENGTH: 27
<212> TYPE: DNA
<213> ORGANISM: Artificial sequence
<220> FEATURE:
<223> OTHER INFORMATION: Synthetic

<400> SEQUENCE: 6
tccaacgatt cgacaaaaac gtccacg                                      27

<210> SEQ ID NO 7
<211> LENGTH: 53
<212> TYPE: DNA
<213> ORGANISM: Artificial sequence
<220> FEATURE:
<223> OTHER INFORMATION: Synthetic

<400> SEQUENCE: 7
ggccagtgct ggagttcgca cgctatattt aaaaaatctc cgtcgacgag ctc        53

<210> SEQ ID NO 8
<211> LENGTH: 27
<212> TYPE: DNA
<213> ORGANISM: Artificial sequence
<220> FEATURE:
<223> OTHER INFORMATION: Synthetic

<400> SEQUENCE: 8
aaagaagtga tccgcgctct gtccacg                                      27
```